Oct. 19, 1954 H. M. TIRET Plant Pat. 1,309
FUCHSIA PLANT
Filed Aug. 4, 1953
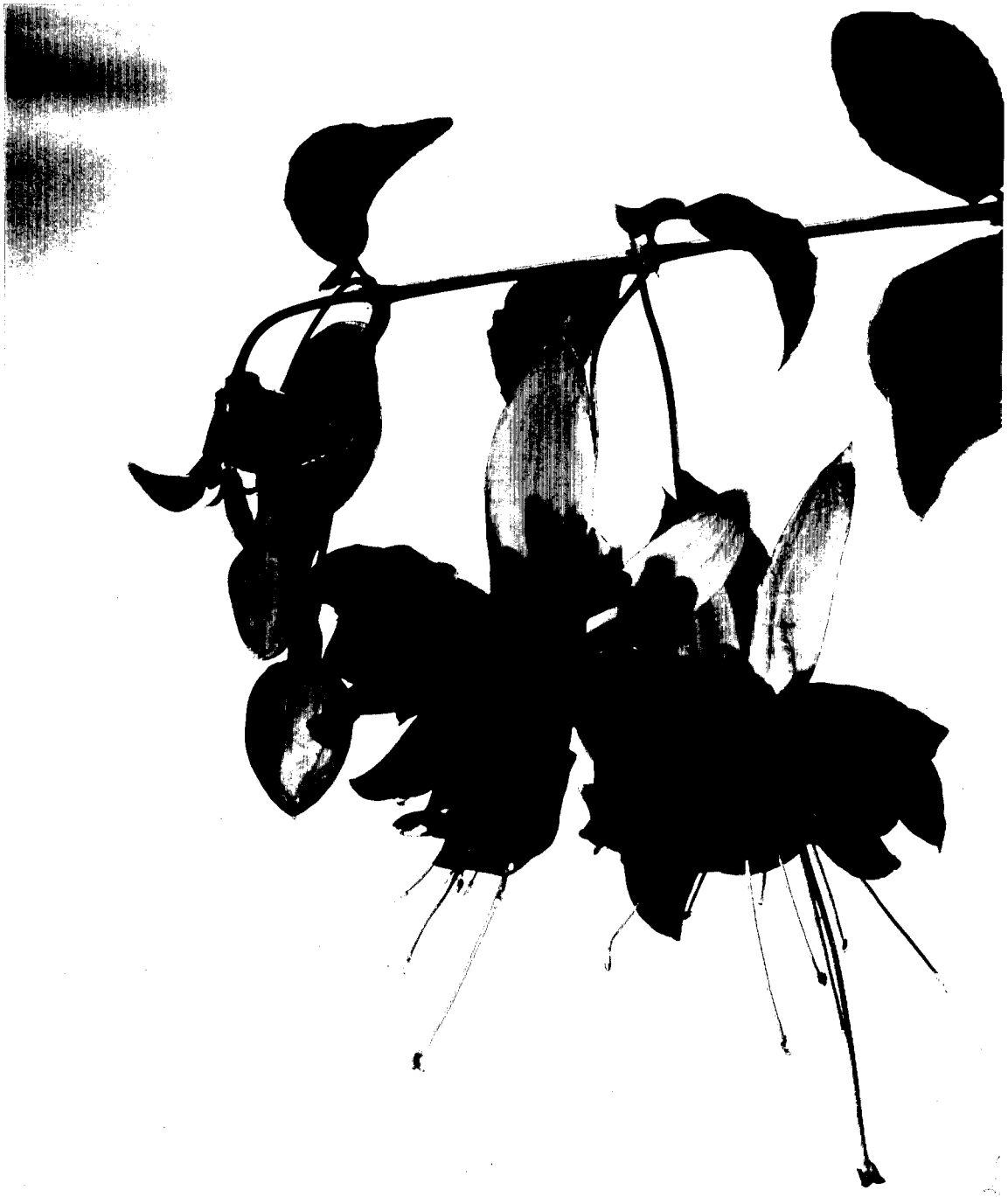
Inventor
Horace M. Tiret Patented Oct. 19, 1954

Plant Pat. 1,309

UNITED STATES PATENT OFFICE 1,309

FUCHSIA PLANT

Horace M. Tiret, San Francisco, Calif.

Application August 4, 1953, Serial No. 372,414

1 Claim. (Cl. 47—60)

This invention relates to a new and improved fuchsia plant, the principal new and different characteristic of which is the unusual, deep purple coloring the petals, having a minimum of red running down from the sepals, in combination with the open, flaring corolla.

The plant was derived as a hybrid from a cross between a seedling (unpatented) not introduced to the trade, namely, 2/24/9, the figures representing applicant's own breeding symbols, and another fuchsia of unknown ancestry. The fuchsia plant is distinguished principally by its green foliage, vigorous, upright habit of growth, with branches tending to stiffness, as contrasted with willowy growth, together with the unusual deep purple coloring of the petals, the minimal red veining from the sepals, and the open, flaring corolla, this combination of form and color not previously existing in any other fuchsia plant. The plant has been asexually reproduced at Palo Alto, California, by cuttings which retained the characteristics of the parent fuchsia.

The plant is an upright variety and grows vigorously, throwing stiff branches during the process of growth. When the plant blooms, the buds open into large double flowers, having a large, loose and flaring form. The major petals are aconite purple (Horticultural Color Chart 937/2), with a very slight currant red veining (Horticultural Color Chart 821/2). The outer surface of the small outer petals has splashes of neyron rose (Horticultural Color Chart 623) running from the base. The tube and sepals are similarly colored currant red (Horticultural Color Chart 821/2). The flower has no fragrance, it is an early bloomer.

In the accompanying drawing, the figure shows a typical branch tip, including both a bud and fully opened blossom, the drawing representing approximately actual size.

A detailed description of this new variety of fuchsia plant follows:

*Habit of growth.*—Strong, upright variety which throws out stiff branches and whose branches are in turn self-branching. Flowers occur both along the stem and at the tips of the branches. The foliage is not dense, which tends to show off the flower to greater advantage.

*Foliage.*—The leaves are medium-large and medium dark green in color. The branches are dark. The mature leaf is not heavily veined, and the serrating of the edges is not pronounced. The outer surface is fairly smooth with a slight crinkly appearance. The underside of the leaf is a lighter green than the topside. The mature leaf measures approximately 3¼ inches in length by 1⅝ inches in width at its widest point.

*Flower.*—The flower is double. The corolla is loosely formed and has a flaring effect. The flower is strongly resistant to wilting at high atmospheric temperatures, but grows equally well in the cooler coastal climate of the western area of the United States. The major petals are a dark purple (aconite purple, Horticultural Color Chart 937/2), with a very slight currant red (Horticultural Color Chart 821/2) veining. This combination of dark purple predominating, minimal red veining, in a loose, flaring corolla, is the outstanding, different and distinctive feature of this plant. The outer surface of the smaller outside petals is splashed with neyron rose (Horticultural Color Chart 623).

*Ovary.*—Dark green, approximately $\frac{7}{16}$ inch in length, and ¼ inch in width at widest point.

*Tube.*—Medium long and medium narrow, length being approximately ⅝ inch, and width $\frac{5}{16}$ inch at widest point. Colored currant red (Horticultural Color Chart 821/2).

*Petals.*—Approximately 27 petals occur to each flower, the petals being loosely formed and flaring. The petals are aconite purple with faint red veining, all as above described.

*Sepals.*—The sepals are four in number, approximately 2½ inches in length and ⅞ inch in width at the widest point. In form, they are broad and recurved when the flower is fully matured. The outer surface is smooth, shiny, and satinlike in texture, the texture of the underside being crepe-like. The color of the sepals is currant red (Horticultural Color Chart 821/2) on both sides.

*Pistil.*—The style is approximately 4 inches in length and $\frac{1}{16}$ inch in width, colored raspberry red. The stigma is pink.

*Stamens.*—The stamens are eight in number, slender, colored dark red with red anther. The length is approximately 2⅛ inches.

*Parentage.*—Applicant's own seedling (unpatented) not introduced to the trade, applicant's breeding symbol 2/24/9, and a fuchsia of unknown ancestry.

It is noted that the foliage and flowers will vary somewhat with the seasons and growing conditions; however, the fuchsia plant is clearly differentiated from others by the aconite purple coloring of the petals, the minimal red veining, and the flaring form.

Having thus disclosed my discovery I claim:

The new and distinct variety of fuchsia plant herein described and illustrated characterized by the aconite purple colouring of the petals, wherein the red veining is reduced to a minimum, in a loose, flaring flower form.

No references cited.